United States Patent [19]
Abe et al.

[11] Patent Number: 5,239,055
[45] Date of Patent: Aug. 24, 1993

[54] PROCESS FOR PURIFYING PERFLUORO(PROPYLVINYLETHER)

[75] Inventors: Masatoshi Abe; Masashi Fukazawa, both of Kitaibaraki; Seiichi Nakamura, Hitachi, all of Japan

[73] Assignee: Nippon Mektron Limited, Tokyo, Japan

[21] Appl. No.: 677,296

[22] Filed: Mar. 29, 1991

[30] Foreign Application Priority Data

Apr. 13, 1990 [JP] Japan ................................. 2-98231

[51] Int. Cl.⁵ .............................................. C08F 6/06
[52] U.S. Cl. .................................... 528/493; 528/501
[58] Field of Search ................... 528/493, 501; 203/62

[56] References Cited

U.S. PATENT DOCUMENTS

| | | | |
|---|---|---|---|
| 3,114,778 | 12/1963 | Fritz | 526/247 |
| 3,132,123 | 5/1964 | Harris et al. | 526/236 |
| 3,250,808 | 5/1966 | Moore | 252/54 |
| 3,321,532 | 5/1967 | Lorenz | 568/615 |
| 3,449,218 | 6/1969 | Jaeger | 203/62 |

FOREIGN PATENT DOCUMENTS 0260773 3/1988 European Pat. Off. .

Primary Examiner—Joseph L. Schofer
Assistant Examiner—Tom Weber
Attorney, Agent, or Firm—Lowe, Price, LeBlanc & Becker

[57] ABSTRACT

Pure perfluoro(propylvinylether) is obtained by extractive distillation of crude perfluoro(propylvinylether) containing a hydrogen fluoride adduct of perfluoro(propylvinylether), which is obtained by gas phase or liquid phase thermal decomposition of perfluoro(2-propoxypropionyl)fluoride, in the presence of a ketone having a boiling point of 100° C. of higher.

7 Claims, No Drawings

PROCESS FOR PURIFYING PERFLUORO(PROPYLVINYLETHER)

BACKGROUND OF THE INVENTION

1. Field of the Invention

This invention relates to a process for purifying perfluoro(propylvinylether) and more particularly to a process for purifying perfluoro(propylvinylether) by effectively separating perfluoro(propylvinylether) from the hydrogen fluoride adduct of perfluoro(propylvinylether).

2. Description of the Prior Art

Perfluoro(propylvinylether) (FPVE) is synthesized from perfluoro(2-propoxypropionyl) fluoride by gas phase thermal decomposition or by liquid phase thermal decomposition according to the following reaction equation (U.S. Pat. Nos. 3,132,123, 3,250,808 and 3,321,532):

The gas phase thermal decomposition is carried out by contacting the raw material perfluoro(2-propoxypropionyl) fluoride with an alkali metal compound such as sodium carbonate in a reaction zone kept at a high temperature such as 300° to 600° C. to thermally decompose the raw material. On the other hand, the liquid phase thermal decomposition is carried out by adding the raw material and an alkali metal compound such as sodium carbonate to a polar organic solvent such as ethyleneglycol, stirring the mixture at room temperature, thereby converting the raw material to an alkali metal salt thereof, and then heating the mixture to a temperature of 110° to 130° C. to thermally decompose the alkali metal.

In any of these thermal decomposition procedures, about 5 to about 10% by weight of heptafluoropropyl-1,2,2,2-tetrafluoroethylether $C_3F_7OCFHCF_3$ is by-produced as a hydrogen fluoride adduct (FPVE.HF) of the product (FPVE) to inevitably contaminate the product (FPVE). Accordingly, European Patent No. 0260773 proposes to control formation of the FPVE.HF by-product by simultaneously using diethyleneglycol dimethylether and dimethylformamide as solvents in the liquid phase thermal decomposition procedure, but its effect has been found not satisfactory.

Most of the by-products can be readily separated and removed by ordinary washing and distillation, but FPVE.HF has a boiling point of 42° C., which is quite near that of FPVE, i.e. 35.5° C. and thus is hard to separate by the ordinary distillation. It may be also possible to convert FPVE.HF to any appropriate derivative and then separate the derivative, but the procedure including the chemical conversion is also hard to carry out and thus is not commercially practicable.

SUMMARY OF THE INVENTION

It is preferable from a commercial viewpoint to use an appropriate solvent to extract any one of FPVE and its HF adduct. An object of the present invention is to provide a process for purifying FPVE by effectively separating FPVE from a HF adduct of FPVE by extractive distillation with a specific solvent.

DETAILED DESCRIPTION OF THE INVENTION

The object of the present invention can be attained by subjecting crude perfluoro(propylvinylether) containing a hydrogen fluoride adduct of perfluoro(propylvinylether) to extractive distillation in the presence of a ketone having a boiling point of 100° C. or higher, thereby purifying perfluoro(propylvinylether).

That is, when a mixture of FPVE and FPVE.HF, usually crude FPVE obtained by the thermal decomposition procedure is subjected to extractive distillation in the presence of a ketone having a boiling point of 100° C. or higher, FPVE and FPVE.HF can be effectively separated from each other.

The ketone for use in the present invention includes, for example, 2-pentanone, 3-pentanone, 2-hexanone, methylisobutylketone, 2-heptanone, 4-heptanone, diisobutylketone, acetonylacetone, mesityl oxide, phorone, isophorone, cyclohexanone, methylcyclohexanone, acetophenone, etc., and particularly preferable are methylisobutylketone, 2-hexanone, 2-heptanone, acetonylacetone and cyclohexanone.

The solvent is used in an amount of about 0.5 to about 50 parts by weight, preferably about 1 to about 10 parts by weight on the basis of one part by weight of FPVE contained in the crude FPVE. When a ketone is used having a boiling point lower than 100° C., the ketone forms an azeotropic mixture with FPVE and thus is not suitable for the extractive distillation.

Extractive distillation is usually carried out in a set of an extractive distillation column and an extracting solvent recovery column. That is, a mixture of FPVE-FPVE.HF as crude FPVE is fed to the extractive distillation column at the lower level position and an extracting solvent is fed thereto at a higher level position to make countercurrent contact of the mixture with the extracting solvent. The component (FPVE) hard to dissolve in the extracting solvent is withdrawn from the extractive distillation column at the column top, whereas the component (FPVE.HF) easy to dissolve in the extracting solvent goes toward the column bottom together with the extracting solvent.

The column bottoms is led to the extracting solvent recovery column operated at a higher temperature and/or under a lower pressure than the temperature and pressure of the extractive distillation column, and the component (FPVE.HF) dissolved in the extracting solvent is stripped off and withdrawn from the extracting solvent recovery column at the column top, while recycling the extracting solvent to the extractive distillation column. The recycle rate of the extracting solvent (feed rate) can be determined in advance from the working curve prepared for the individual extracting solvents.

When the crude FPVE containing FPVE.HF is subjected to extractive distillation in the presence of a ketone having a boiling point of 100° C. or higher, the ketone works to control the evaporation of FPVE.HF and enhance the relative volatity of FPVE, that is, to separate FPVE and FPVE.HF from each other by distillation.

FPVE purified to a high degree by the extractive distillation can be effectively used in the copolymerization reaction with tetrafluoroethylene. It is known that PFA resin, i.e. the copolymer of FPVE and tetrafluoroethylene, can largely improve the moldability of tetrafluoroethylene homopolymer (PTFE resin) that has distinguished heat resistance and solvent resistance, but has a problem in the moldability.

When FPVE to be used as a comonomer in the copolymerization reaction contains a HF adduct of FPVE, the HF adduct acts as a chain transfer agent to give a low molecular weight copolymer. By completely removing the HF adduct, desired PFA resin can be obtained.

The present invention will be explained in detail below, referring to Examples.

PREFERRED EMBODIMENTS OF THE INVENTION

Example 1

1,280 g of a mixture of FPVE-FPVE.HF in a ratio by weight of 93.1:6.9 and 250 g of methylisobutylketone were charged into a 2-1 vessel provided with a vacuum jacket distillation column (diameter: 1.5 cm; height: 140 cm) with a fractionation head filled with a packing material (Helipak packing No. 1).

The vessel was heated to boil the liquid content and at the same time 1,060 g of methylisobutylketone was continuously fed to the distillation column at a level of 100 cm from the bottom of the column at a feed rate of about 1.1 g/min. and so controlled that the total could be always refluxed.

After the column temperature approached the equilibrium state, 275 of initial fraction was withdrawn from the column in a reflux ratio of 60:2 (refluxing: 60 seconds and withdrawal: 2 seconds) over 4 hours, and then at the time when the column top temperature was stabilized to the same temperature as the boiling point of FPVE, 776 g of main fraction was withdrawn in a reflux ratio of 40:2 over 12 hours. The main fraction was assayed by gas chromatography and it was found that FPVE.HF was 0.028% by weight and methylisobutylketone was below the detection limit. Furthermore, it was found that the vapors in the vessel contained 42% by weight of FPVE.HF.

Example 2

Extractive distillation of 1,300 g of a mixture of FPVE-FPVE.HF in a ratio of 85.2:14.8 by weight was carried out in the same manner as in Example 1, while 1,405 g of methylisobutylketone was continuously fed to the extractive distillation column at the same feed rate as in Example 1.

Example 3

Extractive distillation of 1,270 g of a mixture of FPVE-FPVE.HF was carried out in the same manner as in Example 1, except that methylisobutylketone was replaced with acetonylacetone. That is, 1,580 g of acetonylacetone was continuously fed to the extractive distillation column at a feed rate of 1.6 g/min.

Example 4

Extractive distillation of 1,275 g of a mixture of FPVE-FPVE.HF was carried out in the same manner as in Example 1, except that methylisobutylketone was replaced with 2-hexanone. That is, 2,100 g of 2-hexanone was fed to the extractive distillation column at a feed rate of 2.2 g/min.

Example 5

Extractive distillation of 1,270 g of a mixture of FPVE-FPVE.HF was carried out in the same manner as in Example 1, except that methylisobutylketone was replaced with 2-heptanone. But, 2-heptanone was not directly charged into the vessel and total 1,920 g of 2-heptanone was fed to the extractive distillation column at a feed rate of 2.0 g/min.

Example 6

Extractive distillation of 1,270 g of a mixture of FPVE-FPVE.HF was carried out in the same manner as in Example 1, except that methylisobutylketone was replaced with cyclohexane. But, cyclohexanone was not charged directly into the vessel and total 2,100 g of cyclohexanone was supplied to the extractive distillation column at a feed rate of 2.5 g/min.

Results of the foregoing Examples 2 to 6 are summarized in the following Table 1. The solvent in the main fraction was below the detection limit in all the Examples.

TABLE 1

| Ex. No. | Initial fraction (g) | Main fraction (g) | FPVE.HF in main fraction (%) | FPVE.HF in vapors in vessel (%) |
|---|---|---|---|---|
| 2 | 248 | 702 | 0.033 | 54 |
| 3 | 258 | 783 | 0.031 | 45 |
| 4 | 264 | 762 | 0.033 | 42 |
| 5 | 235 | 582 | 0.029 | 34 |
| 6 | 243 | 572 | 0.034 | 36 |

Comparative Example 1

Extractive distillation of 1,260 g of a mixture of FPVE-FPVE.HF was carried out in the same manner as in Example 1 without using the extracting solvent.

Comparative Example 2

Extractive distillation was carried out in the same manner as in Example 1, except that the same amount of methylethylketone was used in place of methylisobutylketone.

Comparative Example 3

Extractive distillation of 1,275 g of a mixture of FPVE-FPVE.HF was carried out in the same manner as in Example 1, except that the same amount of acetonitrile was used in place of methylisobutylketone.

Comparative Example 4

Extractive distillation of 1,275 g of a mixture of FPVE-FPVE.HF was carried out in the same manner as in Example 1, except that the same amount of butyl acetate was used in place of methylisobutylketone.

Comparative Example 5

Extractive distillation was carried out in the same manner as in Example 1, except that the same amount of n-butanol was used in place of methylisobutylketone.

Results of the foregoing Comparative Examples 1 to 5 are summarized in the following Table 2.

TABLE 2

| Comp. Ex. No. | Initial fraction (g) | Main fraction (g) | In main fraction FPVE.HF(%) | In main fraction Solvent(%) |
|---|---|---|---|---|
| 1 | 280 | 725 | 1.5 | — |
| 2 | 272 | 730 | 0.052 | 7.8 |
| 3 | 283 | 710 | 0.35 | 1.1 |
| 4 | 234 | 728 | 0.78 | below detection limit |

TABLE 2-continued

| Comp. Ex. No. | Initial fraction (g) | Main fraction (g) | In main fraction | |
|---|---|---|---|---|
| | | | FPVE.HF(%) | Solvent(%) |
| 5 | 247 | 723 | 1.2 | below detection limit |

What is claimed is:

1. A process for purifying perfluoro(propylvinylether), which comprises subjecting a crude mixture of perfluoro(propylvinylether) and a hydrogen fluoride adduct of perfluoro(propylvinylether) obtained by the gas phase or liquid phase thermal decomposition of perfluoro(2-propoxypropionyl) fluoride to extractive distillation in the presence of a ketone having a boiling point of 100° C. or higher.

2. A process according to claim 1 wherein said ketone is methylisobutyl-ketone, 2-hexanone, 2-heptanone, acetonylacetone or cyclohexanone.

3. A process according to claim 1 wherein said ketone is used in an amount of 0.5 to 50 parts by weight on the basis of one part by weight of the perfluoro(propylvinylether).

4. A process according to claim 1 wherein said ketone is used in an amount of 1 to 10 parts by weight on the basis of one part by weight of the perfluoro(propylvinylether).

5. A process according to claim 1 wherein said extractive distillation is carried out in a set of an extractive distillation column and an extracting solvent recovery column.

6. A process according to claim 1 wherein the extractive distillation is carried out countercurrentwise.

7. A process according to claim 1 wherein said ketone is methylisobutylketone.

* * * * *